US010197566B2

(12) United States Patent
Del Pino González De La Higuera et al.

(10) Patent No.: US 10,197,566 B2
(45) Date of Patent: Feb. 5, 2019

(54) BIOSENSOR COMPRISING METAL NANOPARTICLES

(71) Applicants: UNIVERSIDAD DE ZARAGOZA, Zaragoza (ES); FUNDACIÓN AGENCIA ARAGONESA PARA LA INVESTIGACIÓN Y EL DESARROLLO, Zaragoza (ES); CONSEJO SUPERIOR DE INVESTIGACIONES CIENTÍFICAS, Madrid (ES)

(72) Inventors: Pablo Del Pino González De La Higuera, Zaragoza (ES); Beatriz Pelaz Garcia, Zaragoza (ES); Ester Polo Tobajas, Zaragoza (ES); Valeria Grazú Bonavía, Zaragoza (ES); Jesús Martínez De La Fuente, Zaragoza (ES); Victor Parro Garcia, Zaragoza (ES)

(73) Assignees: UNIVERSIDAD DE ZARAGOZA, Saragossa (ES); FUNDACIÓN AGENCIA ARAGONESA PARA LA INVESTIGACIÓN Y EL DESARROLLO, Saragossa (ES); CONSEJO SUPERIOR DE INVESTIGACIONES CIENTÍFICAS, Sevilla (ES)

( * ) Notice: Subject to any disclaimer, the term of this patent is extended or adjusted under 35 U.S.C. 154(b) by 975 days.

(21) Appl. No.: 14/417,006

(22) PCT Filed: Jul. 26, 2013

(86) PCT No.: PCT/ES2013/070549
§ 371 (c)(1),
(2) Date: Sep. 22, 2015

(87) PCT Pub. No.: WO2014/016465
PCT Pub. Date: Jan. 30, 2014

(65) Prior Publication Data
US 2015/0293084 A1  Oct. 15, 2015

(30) Foreign Application Priority Data
Jul. 26, 2012 (ES) .................................. 201231209

(51) Int. Cl.
| | |
|---|---|
| *G01N 33/543* | (2006.01) |
| *G01N 21/552* | (2014.01) |
| *G01N 21/29* | (2006.01) |
| *G01N 21/78* | (2006.01) |
| *B82Y 15/00* | (2011.01) |

(52) U.S. Cl.
CPC ....... *G01N 33/54386* (2013.01); *G01N 21/29* (2013.01); *G01N 21/554* (2013.01); *G01N 21/78* (2013.01); *G01N 33/54326* (2013.01); *G01N 33/54346* (2013.01); *B82Y 15/00* (2013.01); *G01N 2021/786* (2013.01); *G01N 2201/02* (2013.01); *G01N 2201/06113* (2013.01); *Y10S 977/954* (2013.01)

(58) Field of Classification Search
None
See application file for complete search history.

(56) References Cited

U.S. PATENT DOCUMENTS

| | | | | |
|---|---|---|---|---|
| 4,870,005 | A * | 9/1989 | Akiyoshi | G01N 33/54386 422/421 |
| 6,361,944 | B1 * | 3/2002 | Mirkin | B82Y 5/00 435/6.11 |
| 2011/0059867 | A1 * | 3/2011 | Kim | C07C 233/20 506/16 |

OTHER PUBLICATIONS

Cortie, M. et al., "Plasmonic heating of gold nanoparticles and its exploitation," *Proceedings of SPIE*, vol. 5649, pp. 565-573, 2005.
Haes, A. J. et al., "Detection of a Biomarker for Alzheimer's Disease from Synthetic and Clinical Samples Using a Nanoscale Optical Biosensor," *Journal of the American Chemical Society*, vol. 127, No. 7, pp. 2264-2271, 2005.
International Search Report for PCT/ES2013/070549 dated Jul. 1, 2014.
Liao, H. et al., "Biomedical applications of plasmon resonant metal nanoparticles," *Nanomedicine*, vol. 1, No. 2, pp. 201-208, 2006.
Nearingburg, B. et al., "Characterization of surface plasmon energy transduction in gold nanoparticle/polymer composites by photo-DSC," *Thermochimica Acta*, vol. 512, No. 1-2, pp. 247-253, 2011.
Pelaz, B. et al., "Tailoring the Synthesis and Heating Ability of Gold Nanoprisms for Bioapplications," *Langmuir: The ACS Journal of Surfaces and Colloids*, vol. 28, No. 24, pp. 8965-8970, 2012.
Petryayeva, E. et al., "Localized surface plasmon resonance: Nanostructures, bioassays and biosensing—A review," *Analytica Chimica Acta*, vol. 706, No. 1, pp. 8-24, 2011.
Pissuwan, D. et al., "Functionalised gold nanoparticles for controlling pathogenic bacteria," *Trends in Biotechnology*, vol. 28, No. 4, pp. 207-213, 2010.
Szunerits, S. et al., "Sensing using localised surface plasmon resonance sensors," *Chemical Communication*, vol. 48, No. 72, pp. 8999-9010, 2012.

* cited by examiner

*Primary Examiner* — Ann Y Lam
(74) *Attorney, Agent, or Firm* — McCarter & English, LLP; Jill Ann Mello

(57) ABSTRACT

The present invention discloses a biosensor for visual detection of an analyte, based on the light to heat conversion properties of metal nanoparticles: the analyte is visually detected by the color change in the support areas (where the analyte is present), produced as a result of the heat generated by the metal nanoparticles where they are irradiated with an external light source. Use of said biosensor in a method for the detection of analytes is also claimed.

21 Claims, 10 Drawing Sheets

BIOSENSOR COMPRISING METAL NANOPARTICLES

FIELD OF THE ART

The present invention relates to the field of biotechnology, specifically to the field of biosensors, more specifically to the field of biosensors with metal nanoparticles as a signal transduction system.

BACKGROUND OF THE INVENTION

In recent years, biosensors have been contemplated as analytical alternatives to conventional methods in different fields. A biosensor is an analysis device made up of two fundamental elements: a bioreceptor (an antibody, a DNA probe, or a cell . . . ) prepared to specifically detect a substance, taking advantage of the specificity of biomolecular interactions, and a transducer or sensor, capable of interpreting the biological recognition reaction produced by the receptor and "transducing it" into a quantifiable optical or electrical signal. The most outstanding features of these devices which make them highly attractive options as analytical tools are their specificity, high sensitivity, response capacity leading to a short analysis time, their capacity of being included in integrated systems, ease of automation, capacity of working in real time, their versatility and low cost.

Progress in the field of biosensors lies in the experience acquired throughout the years concerning the recognition capacity and properties of various biomolecules. Many biological instruments ranging from the simplest ones such as enzymes or antibodies to more complex genetic engineering products have been used as recognition elements. On the other hand, the recent advances in microelectronics, nanotechnology and the unique properties of specific materials have been key for such devices.

Despite the foregoing, the current sensing methods are not always capable of meeting the requirements for reliability and speed. The time necessary to perform the assay and the sensitivity of the technique are some of the most significant limitations. Although the development of these devices has mainly been focused on the field of clinical diagnosis, their interest in other fields of application including the environmental, agro-food, chemical, pharmaceutical and military fields is on the rise today.

The present invention proposes a new biosensor based on the light to heat conversion properties of metal nanoparticles.

BRIEF DESCRIPTION OF THE INVENTION

A first aspect of the present invention relates to a biosensor for visual detection of an analyte comprising:
  a. A recognition molecule (capture biomolecule) capable of recognizing the target analyte;
  b. A support with a heat sensitive surface where the recognition molecule of step a) is immobilized or found to be immobilized;
  c. An external light source;
  d. A second recognition molecule (detection biomolecule) capable of recognizing the target analyte; and
  e. A metal nanoparticle having a surface plasmon band;
where the analyte is visually detected by the color change in the support areas where the analyte is present, produced as a result of the heat generated by the metal nanoparticles when they are irradiated with the external light source.

In a preferred embodiment of the first aspect of the invention, the biosensor for visual detection of an analyte comprises:
  a. A recognition molecule (capture biomolecule) capable of recognizing the target analyte, immobilized on a support with a heat sensitive surface;
  b. An external light source; and
  c. A second recognition molecule (detection biomolecule) capable of recognizing the target analyte, bound to the surface of a metal nanoparticle having a surface plasmon band;
where the analyte is visually detected by the color change in the support areas where the analyte is present, produced as a result of the heat generated by the metal nanoparticles when they are irradiated with the external light source.

A second aspect of the present invention relates to a biosensor for visual detection of an analyte comprising:
  a. A recognition molecule (capture biomolecule) capable of recognizing the target analyte;
  b. A support with a heat sensitive surface;
  c. An external light source;
  d. A second recognition molecule (detection biomolecule) capable of recognizing the target analyte, optionally bound to a label molecule; and
  e. Metal nanoparticles with a surface plasmon band functionalized with biomolecules specifically recognizing the detection biomolecule or the label molecule with which the detection biomolecule was modified;
where the analyte is visually detected by the color change in the support areas where the analyte is present, produced as a result of the heat generated by the metal nanoparticles when they are irradiated with the external light source.

A third aspect of the present invention relates to a biosensor for visual detection of an analyte as defined in the second aspect of the invention, comprising:
  a. A recognition molecule (capture biomolecule) capable of recognizing the target analyte;
  b. A support with a heat sensitive surface;
  c. An external light source;
  d. A second recognition molecule (detection biomolecule) capable of recognizing the target analyte, bound to one or several biotin molecules; and
  e. Metal nanoparticles with a surface plasmon band functionalized with streptavidin molecules, avidin molecules or the like, specifically recognizing the biotin molecules;
where the analyte is visually detected by the color change in the support areas where the analyte is present, produced as a result of the heat generated by the metal nanoparticles when they are irradiated with the external light source.

A fourth aspect of the present invention relates to a biosensor for visual detection of an analyte as defined in the second aspect of the invention, comprising:
  a. A recognition molecule (capture biomolecule) capable of recognizing the target analyte;
  b. A support with a heat sensitive surface;
  c. An external light source;
  d. A second recognition molecule where the molecule is an antibody (detection antibody) capable of recognizing the target analyte; and
  e. Metal nanoparticles with a surface plasmon band functionalized with anti-Fc antibodies binding to the detection antibody;
where the analyte is visually detected by the color change in the support areas where the analyte is present, produced as a result of the heat generated by the metal nanoparticles when they are irradiated with the external light source.

In a particular embodiment of any of the aspects of the invention, the recognition molecules (capture and detection biomolecules) are selected from the list consisting of antibodies, peptides, enzymes, polysaccharides, nucleic acids (DNAs, RNAs), aptamers or peptide nucleic acids (PNAs), preferably DNA molecules and antibodies.

In another embodiment of any of the aspects of the invention, the external light source is a laser, where the laser has a wavelength equal to the wavelength of the maximum of the surface plasmon band of the metal nanoparticle.

In another embodiment of any of the two aspects of the invention, the metal nanoparticle is selected from the list consisting of:
  a. Gold nanoparticles;
  b. Silver nanoparticles; or
  c. Copper nanoparticles The metal nanoparticle is preferably a triangular gold nanoprism.

In another embodiment of any of the two aspects of the invention, the surface of the support comprises a heat sensitive paper or a cellulose membrane, cellulose nitrate membrane or cellulose acetate membrane. Preferably, the heat sensitive paper has adhered thereto a second support selected from the list consisting of glass, silicon, ceramic, polystyrene, cellulose membrane, cellulose nitrate membrane or cellulose acetate membrane.

A fifth aspect of the present invention relates to the use of a biosensor according to the first aspect of the invention for visual detection of an analyte which comprises:
  a. Adding the sample where the analyte to be determined is present to a support with the analyte recognition molecule (capture biomolecule) immobilized thereon;
  b. Incubating the support of step a) with metal nanoparticles functionalized with a second analyte recognition molecule (detection biomolecule); and
  c. Optionally placing the support on a heat sensitive surface if the support does not already comprise said surface; and
  d. Irradiating the support of step b) or c) with the external light source.

A sixth aspect of the invention relates to the use of a biosensor for visual detection of an analyte as defined in the second aspect of the invention, for the detection of an analyte which comprises:
  a. Adding the sample where the analyte to be determined is present to a support with the analyte recognition molecule (capture biomolecule) immobilized thereon;
  b. Incubating the support of step a) with a second analyte recognition molecule (detection biomolecule) optionally tagged with a label;
  c. Incubating the support of step b) with metal nanoparticles functionalized with a biomolecule specifically recognizing the detection biomolecule or the label with which the detection biomolecule was modified; and
  d. Optionally placing the support on a heat sensitive surface if the support does not already comprise said surface; and
  e. Irradiating the support of step c) or d) with the external light source.

A preferred embodiment of the sixth aspect of the invention relates to the use of a biosensor for the detection of an analyte which comprises:
  a. Adding the sample where the analyte to be determined is present to a support with the analyte recognition molecule (capture biomolecule) immobilized thereon;
  b. Incubating the support of step a) with a second analyte recognition molecule (detection biomolecule) tagged with at least one biotin molecule;
  c. Incubating the support of step b) with metal nanoparticles functionalized with streptavidin; and
  d. Optionally placing the support on a heat sensitive surface if the support does not already comprise said surface; and
  e. Irradiating the support of step c) or d) with the external light source.

Another preferred embodiment of the sixth aspect of the invention relates to the use of a biosensor for the detection of an analyte which comprises:
  a. Adding the sample where the analyte to be determined is present to a support with the analyte recognition molecule (capture biomolecule) immobilized thereon;
  b. Incubating the support of step a) with a second recognition molecule (detection biomolecule) which will be an antibody;
  c. Incubating the support of step b) with metal nanoparticles functionalized with an anti-Fc antibody; and
  d. Optionally placing the support on a heat sensitive surface if the support does not already comprise said surface; and
  e. Irradiating the support of step c) or d) with the external light source.

A seventh aspect of the invention relates to the use of a biosensor as defined in the first aspect of the invention for the detection of an analyte which comprises:
  a. Adding to a sample where the analyte to be determined is present metal nanoparticles functionalized with a second analyte recognition molecule (detection biomolecule);
  b. Extracting the analyte bound to the nanoparticles from the sample of step a) preferably through a centrifugation process;
  c. Adding the extraction of step b to a support with the analyte recognition molecule (capture biomolecule) immobilized thereon;
  d. Optionally placing the support on a heat sensitive surface if the support does not already comprise said surface; and
  e. Irradiating the support of step c) or d) with the external light source.

An eighth aspect of the present invention relates to the use of a biosensor according to any of the preceding aspects or embodiments for the detection of additives, drugs, pathogenic microorganisms, food components, pesticides, toxic compounds or in the analysis of biochemical oxygen demand.

BRIEF DESCRIPTION OF THE DRAWINGS

FIG. 2.

FIG. 3.

FIG. 5 shows anti-CEA antibody 3C1+CEA+anti-CEA antibody 3C6-gold nanoprisms recognition with different irradiation times and different distances between the surface and the laser.

DESCRIPTION OF THE INVENTION

Figure 1:
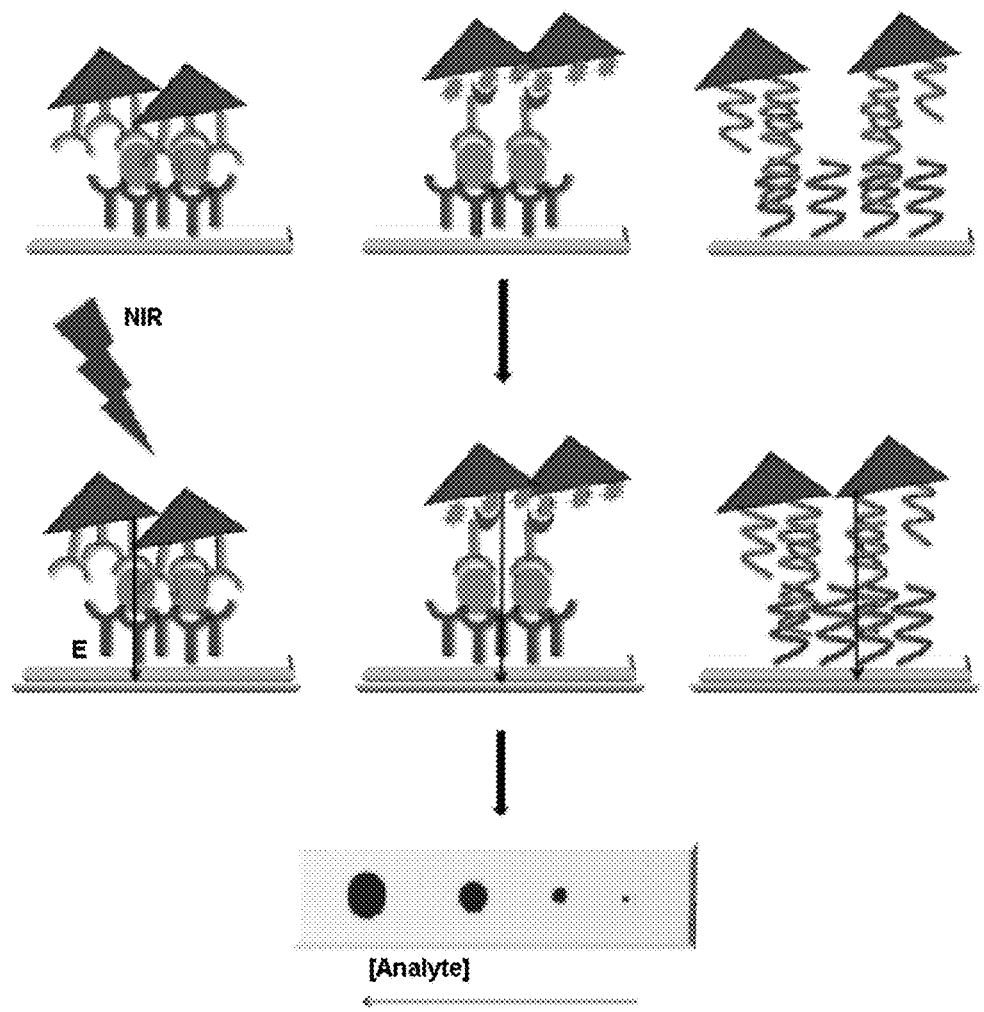
FIG. 1 shows the diagram of the recognition system of the present invention.

The present invention relates to a biosensor comprising (i) a recognition molecule (capture biomolecule) capable of recognizing the target analyte; (ii) a support with a heat sensitive surface; (iii) an external light source; (iv) a second recognition molecule (detection biomolecule) capable of recognizing the target analyte and (v) a metal nanoparticle having a surface plasmon band, characterized in that the analyte is visually detected by the color change in the support areas where the analyte is present, produced as a result of the heat generated by the metal nanoparticles when they are irradiated with the external light source.

The biosensor of the present invention uses the light to heat conversion properties of metal nanoparticles as a signal transduction system. The basis for using this system as a tag in biosensors is due to the presence of the surface plasmon absorption band. These absorption bands are produced when the frequency of the light striking the nanoparticle is in resonance with the collective oscillation frequency of the electrons in the particle conduction band, causing excitation. This phenomenon is known as "localized surface plasmon resonance" (LSPR). The position in the spectrum of the resonance band greatly depends on the particle shape, size and structure (hollow or solid), as well as on the dielectric medium where the particle is found. LSPR leads to high molar extinction coefficients ($\sim 3 \times 10^{11}$ $M^{-1}$ $cm^{-1}$), with an efficiency equivalent to 106 fluorophore molecules and a significant increase in the local electric field close to the nanoparticle.

Metal nanoparticles such as gold, silver or copper nanoparticles have this surface plasmon resonance effect. When irradiated with a high intensity external light source with the suitable frequency, such as a laser, these particles are capable of releasing part of the absorbed energy in the form of heat, causing a localized temperature increase around their surface.

This controlled heat generation is the basis of the new detection system which has been developed. This generated heat causes a perceptible change in a suitably selected heat sensitive surface. In this sense, the inventors of the present invention have discovered that, surprisingly, a detection limit of the order of picograms is obtained in the experiments conducted using the color change in the support areas where the analyte is present, produced by the metal nanoparticles when they are irradiated with the external light source as the detection means. Therefore, Example 4 of the present invention illustrates how a detection limit was obtained using the visual detection of the present invention, said limit having a lower order, and therefore a greater sensitivity, than that achieved in the experiments conducted using an infrared camera as the detection means. This surprising result gave rise to the development of a biosensor having the following features: (i) high sensitivity, (ii) high selectivity or specificity, so that the biosensor interacts exclusively with the analyte of interest and not with other analytes having similar properties; (iii) high reliability so that there will be no noise problems in the transduction system due to the sample to be analyzed; (iv) low production cost; (v) short analysis time which enables prompt actions if necessary; (vi) sample pretreatment is unnecessary, which entails time, material and reagent savings; (vii) simple handling so that no qualified personnel is required to use the biosensor; (viii) capacity to perform the analyses in real time, and (ix) portable to enable performing in situ analysis.

Therefore, a first aspect of the present invention relates to a biosensor for visual detection of an analyte comprising:
    a. A recognition molecule (capture biomolecule) capable of recognizing the target analyte;
    b. A support with a heat sensitive surface where the recognition molecule (capture biomolecule) of step a) is immobilized thereon;
    c. An external light source;
    d. A second recognition molecule (detection biomolecule) capable of recognizing the target analyte; and
    e. A metal nanoparticle having a surface plasmon band;
where the analyte is visually detected by the color change in the support areas where the analyte is present, produced as a result of the heat generated by the metal nanoparticles when they are irradiated with the external light source.

Emphasis must be made on the fact that in the context of the present invention visual detection is understood as any detection that can be distinguished by the naked eye without needing to use any type of instrumentation for detection such as an infrared camera.

Therefore, in a preferred embodiment of the first aspect of the invention the biosensor for visual detection of an analyte comprises:
    a. A recognition molecule (capture biomolecule) capable of recognizing the target analyte;
    b. A support with a heat sensitive surface where the recognition molecule (capture biomolecule) of step a) is immobilized thereon;
    c. An external light source;
    d. A second recognition molecule (detection biomolecule) capable of recognizing the target analyte; and
    e. A metal nanoparticle having a surface plasmon band;
where the biosensor does not comprise any type of instrumentation capable of detecting the light to heat conversion of the metal nanoparticles when they are irradiated with the external light source.

In another preferred embodiment of the first aspect of the invention, the biosensor comprises:
    a. A recognition molecule (capture biomolecule) capable of recognizing the target analyte, immobilized on a support with a heat sensitive surface;
    b. An external light source; and
    c. A second recognition molecule (detection biomolecule) capable of recognizing the target analyte, bound to the surface of a metal nanoparticle having a surface plasmon band;
where the analyte is visually detected by the color change in the support areas where the analyte is present, produced as a result of the heat generated by the metal nanoparticles when they are irradiated with the external light source.

In the context of the present invention, external light source is understood as any electromagnetic radiation source with energy between 380 nm and 1100 nm, with the capacity to cause excitation of the LSPR band of metal particles based on gold, silver, copper or any of their alloys or oxidized states, preferably in the near infrared range (between 750 and 1100 nm) because energy absorption by the interfering biomolecules present in the sample which absorb in the visible range of the spectrum (hemoglobin, etc.) does not occur in that energy range. The external light source can be a monochromatic or polychromatic light source, preferably a monochromatic light source.

In the context of the present invention, metal nanoparticle having a surface plasmon band is understood as any mono- or polycrystalline cluster of metal atoms in any of their oxidation states, or any of their alloys, having all geometric dimensions between 1 and 1000 nm, preferably between 1 and 200 nm. In a preferred embodiment of the invention, said metal atoms are noble metals. In a more preferred embodiment of the invention, said metal atoms are gold, silver or copper atoms. In an even more preferred embodiment of the invention, they are tubular or triangular gold or silver atoms.

In the context of the present invention, recognition molecule or capture biomolecule is understood as any molecule capable of specifically recognizing a specific analyte through any type of chemical or biological interaction.

In the context of the present invention, second recognition molecule or detection biomolecule is understood as any molecule capable of specifically recognizing a specific analyte through any type of chemical or biological interaction.

The molecules used as recognition elements in the biosensors of the present invention must have a sufficiently selective affinity for recognizing a specific analyte in the presence of other compounds, in addition to being stable over time and preserving their structure as well as their biological activity once immobilized on the support and on the surface of the nanoparticles.

Antibodies, peptides, enzymes, proteins, polysaccharides, nucleic acids (DNAs), aptamers or peptide nucleic acids (PNAs) can be used as recognition molecules in the developed system.

In most cases, the most widely used bioreceptors are nucleic acids, antibodies or antibody fragments, antibodies or antibody fragments being those which have given rise to the highest number of techniques useful for diagnosis. The reason lies in the flexibility of the immune system to produce a virtually unlimited amount of antibodies with different selectivities and a high affinity for their corresponding antigen. Today, it is possible to obtain monoclonal antibodies or antibody fragments from virtually any molecule regardless of size. On the other hand, one of the advantages offered by the antibodies is the structural homogeneity of these proteins, which is independent of their specificity. This allows standardizing methods related to the use thereof as immunochemical reagents, such as the preservation or immobilization thereof on the surface of the transducer. Antibody fragments (Fab or single-chain Fv fragment) preserving the structure and the antigen recognition capacity, as well as recombinant antibodies, such as second generation monoclonal antibodies or minibodies, can be prepared as recognition molecules by means of using molecular biology techniques.

On the other hand, aptamers are molecules which can replace antibodies in certain applications due to their small size and low immunogenicity. Aptamers are single-stranded nucleic acids having well-defined three-dimensional shapes allowing them to bind to the target molecule in a manner similar to the antibodies. Aptamers combine the optimum features of small molecules (low immunogenicity, high diffusion, etc.) and of antibodies (high specificity and affinity, and chemical stability). Another advantage with respect to monoclonal antibodies is that they are chemically synthesized instead of being biologically expressed.

Nucleic acids are capable of detecting variations in a single base in a complementary DNA sequence. They can be used in gene sequencing processes, gene expression analysis and in the detection of DNA mutations and alterations associated with specific diseases, since it is possible to synthetically construct nucleotide sequences corresponding to the structure of previously identified genes. Today, the use thereof is being replaced by PNA strands because they have a higher biological stability (against degradation by various enzymes) and chemical stability (more resistant to variations in pH or ionic force). Furthermore, since unlike DNA they contain neither 2'-deoxy-D-ribose units nor phosphodiester bonds, they have a neutral structure which reduces electrostatic repulsion during hybridization, establishing stronger bonds; in addition to having a lower non-specific adsorption.

The recognition element (capture biomolecule) of the sensor will normally be immobilized on a support with a heat sensitive surface by physical retention inside a matrix (entrapment), physical adsorption on a matrix by means of ionic or hydrophobic interactions, or binding by means of covalent bond.

In this sense, in the context of the present invention support with a heat sensitive surface is understood as any surface capable of experiencing a structural change when heated, resulting in image development. Thermal paper which will give rise to a development signal after being subjected to a temperature increase due to its heat sensitivity will preferably be used as the heat sensitive surface. Thermal paper is considered as any paper having a thermal layer incorporating a dye, a sensitizer and a color developer (regardless of the chemical components with which it has been prepared) capable of reacting with one another giving rise to an image after being subjected to a temperature increase. In another preferred embodiment, any smart polymer which, after being subjected to an external stimulus such as temperature change, gives rise to a response in the polymer properties such as: contraction, bending, color change, state change, luminescence, etc., will be used as the heat sensitive surface. The types of temperature sensitive polymers include: PNIPAM, poly(N-isopropylacrylamide), poly(N-vinylpiperidine) or poly(N-vinylcaprolactam).

In one embodiment of the invention, the support with a heat sensitive surface of the system comprises at least one heat sensitive support where molecular recognition takes place, such as a membrane made of cellulose or derivatives thereof (cellulose nitrate, cellulose acetate, etc) or heat sensitive paper.

In another embodiment of the invention, the support with a heat sensitive surface of the system comprises two supports. A first support where the capture biomolecule will be immobilized, and said support is a membrane made of cellulose or derivatives thereof (cellulose nitrate, cellulose acetate, etc), or other materials such as polystyrene, ceramic, silicon or glass. A second support consisting of a heat sensitive surface which will give rise to the development signal after being subjected to a temperature increase will be adhered to this first support.

A second aspect of the present invention relates to a biosensor for visual detection of an analyte comprising:
  a. A recognition molecule (capture biomolecule) capable of recognizing the target analyte;
  b. A support with a heat sensitive surface;
  c. An external light source;
  d. A second recognition molecule (detection biomolecule) capable of recognizing the target analyte, optionally bound to a label molecule; and e. Metal nanoparticles with a surface plasmon band functionalized with biomolecules specifically recognizing the detection biomolecule or the label with which the detection biomolecule was modified;

where the analyte is visually detected by the color change in the support areas where the analyte is present produced as a result of the heat generated by the metal nanoparticles when they are irradiated with the external light source. Again it is noted that visual detection is understood as any detection that can be distinguished by the naked eye without needing to use any type of instrumentation for detection such as an infrared camera. Therefore, the biosensor of the second aspect of the invention does not comprise any type of instrumentation capable of detecting light to heat conversion of the metal nanoparticles when they are irradiated with the external light source.

In the context of the present invention label molecules are understood as those molecules that are recognized by affinity for a ligand-protein type interaction or for molecular recognition by hybridization between nucleic acid strands. In the first case it is understood that the detection biomolecule is modified with an antigen, hormone, vitamin, polyhistidine tag, or lectin domains, among others. It is therefore understood that the NPs are functionalized with antibodies, aptamers, receptors, binding proteins, tricarboxylic acids modified with divalent metal ions, or sugars capable of interacting specifically with the label of the detection biomolecule, respectively. In the second case it is understood that both the detection biomolecule and the gold NP are functionalized with complementary strands of naturally occurring nucleic acids (deoxyribonucleic acid or DNA, ribonucleic acid or RNA) or artificial nucleic acids (peptide nucleic acid or PNA, morpholines, etc.) or combinations of both (DNA-DNA, PNA-DNA, DNA-PNA, PNA-PNA, etc)

A third aspect of the present invention relates to a biosensor for visual detection as defined in the second aspect of the invention, comprising:
   a. A recognition molecule (capture biomolecule) capable of recognizing the target analyte;
   b. A support with a heat sensitive surface;
   c. An external light source;
   d. A second recognition molecule (detection biomolecule) capable of recognizing the target analyte bound to one or several biotin molecules; and
   e. Metal nanoparticles with a surface plasmon band functionalized with streptavidin molecules, avidin molecules or the like, specifically recognizing the biotin molecules;

where the analyte is visually detected by the color change in the support areas where the analyte is present produced as a result of the heat generated by the metal nanoparticles when they are irradiated with the external light source.

A fourth aspect of the present invention relates to a biosensor for visual detection as defined in the second aspect of the invention, comprising:
   a. A recognition molecule (capture biomolecule) capable of recognizing the target analyte;
   b. A support with a heat sensitive surface;
   c. An external light source;
   d. A second recognition molecule (detection antibody) capable of recognizing the target analyte; and
   e. Metal nanoparticles with a surface plasmon band functionalized with anti-Fc or anti-IgG antibodies binding to the detection antibody;

where the analyte is visually detected by the color change in the support areas where the analyte is present produced as a result of the heat generated by the metal nanoparticles when they are irradiated with the external light source.

The proposed device is a "sandwich" type recognition system, between a "recognition" molecule, capture biomolecule (whether it is a protein such as an antibody, a DNA probe, PNA probe, etc.), immobilized on the support where analyte recognition will take place, and a second detection molecule, detection biomolecule, (a second antibody, or a complementary DNA probe) bound to the surface of the metal nanoparticle, whether directly or indirectly through the reader protein and/or label. By functionalizing the supports and the nanoparticles with the corresponding recognition molecules, a number of analytes can be detected following the same strategy.

Additionally, the second to the fourth aspects the present invention specifically relate to a universal detection system. In fact, according to the third aspect of the invention it is verified how by using biotin-labeled detection biomolecules and functionalizing the metal nanoparticles with streptavidin, the same nanoparticles conjugated with this protein can be used for different analyte recognition based on the avidin-biotin interaction, thereby preventing having to prepare the nanoparticle-detection biomolecule conjugate for each analyte to be determined. Another example would be the fourth aspect of the invention, where a detection system based on functionalizing the metal nanoparticles with an anti-Fc antibody capable of recognizing the Fc region of any other antibody could use the same nanoparticles for different analyte recognition, provided that the detection biomolecule of this system is an antibody.

Therefore, the device of the present invention allows analyzing multiple samples in a single assay with a sensitivity limit of the order of picograms.

In a merely illustrative embodiment of the present invention, the detection of an analyte in a specific sample can be carried out by immobilizing the recognition molecule (capture biomolecule) in a first step on a support, for example on a cellulose nitrate membrane. Then a second step is carried out by adding the sample where the analyte to be determined is present to the support, being left enough time for the antigen-antibody recognition to occur. Finally in a third step, the support is incubated with the nanoparticles functionalized with the second recognition molecule (detection biomolecule). After molecular recognition, the support is placed on a heat sensitive surface, provided that the support does not already have a heat sensitive surface, for being irradiated with the external light source, for example a near infrared emitting laser, the analyte thus being detected.

In the case of the second to the fourth aspects of the present invention, the assay consists of an additional step. For example, in the case of using the device as defined in the third aspect of the invention, in the third step the support is incubated with a solution of the recognition molecule (detection biomolecule), for example a biotin-labeled secondary antibody. After performing the corresponding washings, a fourth step of incubation with the nanoparticles functionalized with streptavidin is carried out, to finally irradiate the support with the emitting laser once the excess nanoparticles are washed out of said support.

In the case of the fourth aspect of the invention where the nanoparticle has been functionalized with anti-Fc antibodies after the step of incubation with the sample, to capture the analyte to be determined, a third step of incubation with an antibody as the detection biomolecule is carried out. After performing the corresponding washings, in a fourth step the nanoparticles functionalized with the anti-Fc antibody are added, to finally irradiate the support with the emitting laser once said support is washed.

A possibility for improving the detection limit of the biosensor of the present invention consists of first performing analyte recognition in the sample by adding the functionalized nanoparticles directly on the sample. Therefore, once the antigen-antibody recognition has taken place, the analyte with the nanoparticles can be extracted by means of centrifugation. This step allows concentrating the analyte regardless of the sample volume and allows extracting the analyte from the remaining components of the sample where it is found. The rest of the method would be performed in the same way as described above, once the nanoparticles with the analyte are recovered, they would be incubated with the sensing surface where the recognition molecule has been immobilized.

Therefore, with the described biosensor based on the properties of the metal nanoparticles with a surface plasmon band as the transduction system (in the surface plasmon resonance effect), it is possible to detect various analytes directly in a sample quickly and selectively at very low concentrations, of the order of picograms.

On the other hand, the present invention also relates to biosensors useful in non-exclusively visual analyte detection methods. Specifically, the present invention relates to a biosensor (hereinafter "thermopile biosensor 1") comprising:
  a. A recognition molecule (capture biomolecule) capable of recognizing the target analyte;
  b. A support where the recognition molecule of step a) is immobilized;
  c. An external light source;
  d. A second recognition molecule (detection biomolecule) capable of recognizing the target analyte;
  e. A thermopile; and
  f. A metal nanoparticle having a surface plasmon band;
where the analyte is detected when the thermopile detects light to heat conversion of the metal nanoparticles when they are irradiated with the external light source.

Figure 8:
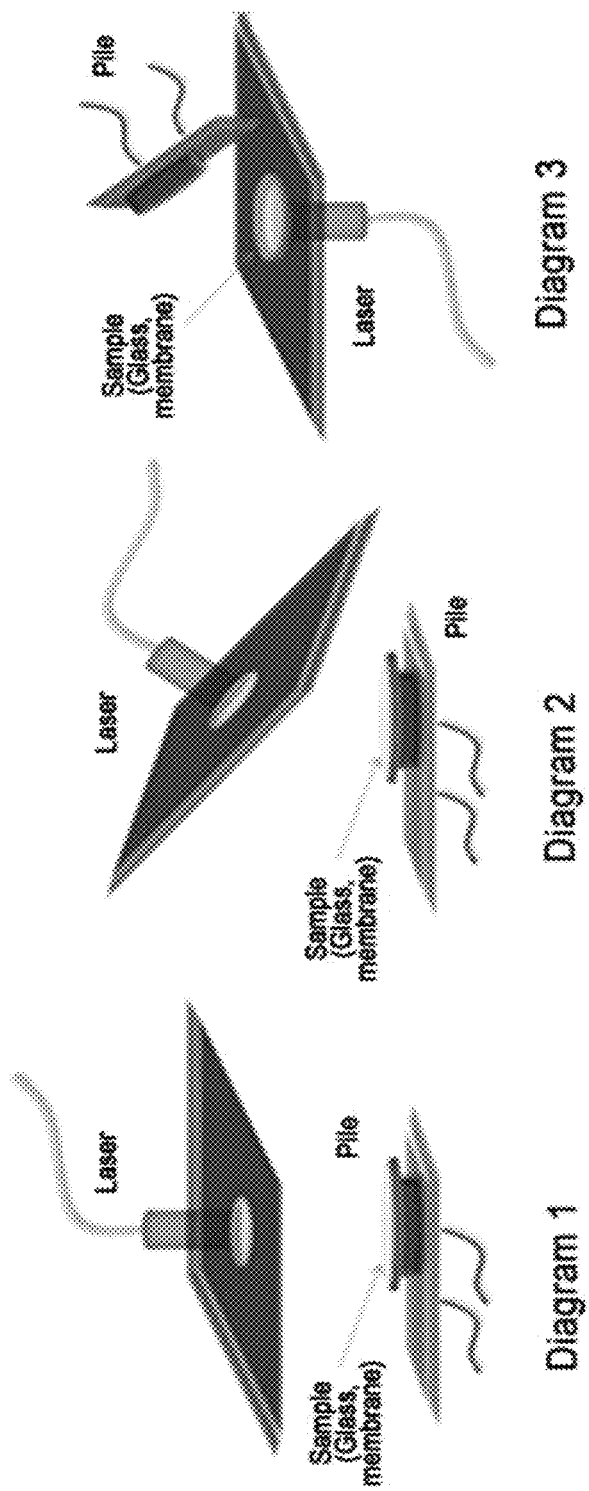
FIG. 8 shows the three design diagrams of the biosensor described in Example 5.

The assembly of this type of biosensor is illustrated in FIG. 8 and in Example 5.

In another preferred embodiment of the invention, the thermopile biosensor 1 comprises:
  a. A recognition molecule (capture biomolecule) capable of recognizing the target analyte, immobilized on a support with a heat sensitive surface;
  b. An external light source; and
  c. A second recognition molecule (detection biomolecule) capable of recognizing the target analyte, bound to the surface of a metal nanoparticle having a surface plasmon band.

Another aspect of the present invention relates to a biosensor (hereinafter "thermopile biosensor 2") comprising:
  a. A recognition molecule (capture biomolecule) capable of recognizing the target analyte;
  b. A support;
  c. An external light source;
  d. A second recognition molecule (detection biomolecule) capable of recognizing the target analyte, optionally bound to a label molecule;
  e. A thermopile; and
  f. Metal nanoparticles with a surface plasmon band functionalized with biomolecules specifically recognizing the detection biomolecule or the label with which the detection biomolecule was modified
where the analyte is detected when the thermopile detects light to heat conversion of the metal nanoparticles when they are irradiated with the external light source.

An additional aspect of the present invention relates to the thermopile biosensor 2 as it has been defined, comprising:
  a. A recognition molecule (capture biomolecule) capable of recognizing the target analyte;
  b. A support;
  c. An external light source;
  d. A second recognition molecule (detection biomolecule) capable of recognizing the target analyte bound to one or several biotin molecules;
  e. A thermopile; and
  f. Metal nanoparticles with a surface plasmon band functionalized with streptavidin molecules, avidin molecules or the like, specifically recognizing the biotin molecules.

Another additional aspect of the present invention relates to the thermopile biosensor 2 as it has been defined, comprising:
  a. A recognition molecule (capture biomolecule) capable of recognizing the target analyte;
  b. A support;
  c. An external light source;
  d. A second recognition molecule (detection antibody) capable of recognizing the target analyte;
  e. A thermopile; and
  f. Metal nanoparticles with a surface plasmon band functionalized with anti-Fc or anti-IgG antibodies binding to the detection antibody.

The proposed device is a "sandwich" type recognition system between a "recognition" molecule, capture biomolecule (whether it is a protein such as an antibody, a DNA probe, PNA probe, etc.), immobilized on the support where analyte recognition will take place, and a second detection molecule, detection biomolecule, (a second antibody or a complementary DNA probe) bound to the surface of the metal nanoparticle whether directly or indirectly through the reader protein and/or label. By functionalizing the supports and the nanoparticles with the corresponding recognition molecules, a number of analytes can be detected following the same strategy.

Additionally, the last two aspects of the present invention specifically relate to a universal detection system. In fact, according to these aspects of the invention it can be verified how by using biotin-labeled detection biomolecules and functionalizing the metal nanoparticles with streptavidin, the same nanoparticles conjugated with this protein can be used for different analyte recognition based on avidin-biotin interaction, thereby preventing having to prepare the nanoparticle-detection biomolecule conjugate for each analyte to be determined. The detection system based on functionalizing the metal nanoparticles with an anti-Fc antibody capable of recognizing the Fc region of any other antibody could use the same nanoparticles for different analyte recognition, provided that the detection biomolecule of this system is an antibody.

Furthermore, the present invention relates to the following analyte detection methods.

(1) Method for the detection of an analyte which comprises:
  a. Adding the sample where the analyte to be determined is present to a support with the analyte recognition molecule (capture biomolecule) immobilized thereon;

b. Incubating the support of step a) with metal nanoparticles functionalized with a second analyte recognition molecule (detection biomolecule);
c. Irradiating the support of step b) or c) with the external light source; and
d. Detecting the analyte by using a thermopile capable of detecting light to heat conversion of the metal nanoparticles when they are irradiated with the external light source.

(2) Method for the detection of an analyte which comprises:
a. Adding the sample where the analyte to be determined is present to a support with the analyte recognition molecule (capture biomolecule) immobilized thereon;
b. Incubating the support of step a) with a second analyte recognition molecule (detection biomolecule) bound to at least one label molecule;
c. Incubating the support of step b) with metal nanoparticles functionalized with at least one molecule binding specifically to the label;
d. Irradiating the support of step c) or d) with the external light source; and
e. Detecting the analyte by using a thermopile capable of detecting light to heat conversion of the metal nanoparticles when they are irradiated with the external light source.

In a preferred embodiment of the method indicated above, the label molecule is biotin and the molecule binding specifically to the label is avidin or streptavidin or the label molecule is avidin or streptavidin and the molecule binding specifically to the label is biotin.

(3) Method for the detection of an analyte which comprises:
a. Adding the sample where the analyte to be determined is present to a support with the analyte recognition molecule (capture biomolecule) immobilized thereon;
b. Incubating the support of step a) with a second recognition molecule (detection biomolecule) which is a detection antibody;
c. Incubating the support of step b) with metal nanoparticles functionalized with anti-Fc antibodies;
d. Irradiating the support of step c) with the external light source and
e. Detecting the analyte by using a thermopile capable of detecting light to heat conversion of the metal nanoparticles when they are irradiated with the external light source.

(4) Method for the detection of an analyte which comprises:
a. Adding to a sample where the analyte to be determined is present metal nanoparticles functionalized with a second analyte recognition molecule (detection biomolecule);
b. Extracting the analyte with the nanoparticles from the sample of step a);
c. Adding the extraction of step b to a support with the analyte recognition molecule (capture biomolecule) immobilized thereon;
e. Irradiating the support of step c) with the external light source; and
f. Detecting the analyte by using a thermopile capable of detecting light to heat conversion of the metal nanoparticles when they are irradiated with the external light source.

The biosensors of the present invention can be used but without any limitation whatsoever for the detection of additives, drugs, pathogenic microorganisms, food components, pesticides, toxic compounds or in the analysis of the biochemical oxygen demand. The biosensors of the present invention can be used for the detection of any type of analyte both qualitatively and quantitatively.

The following examples serve to merely illustrate the present invention.

EXAMPLES

Example 1

Synthesis of Metal Nanoparticles

Synthesis of gold nanoparticles: The synthesis of gold nanoparticles was carried out following the method described by Turkevich et al. "*A study of the nucleation and growth processes in the synthesis of colloidal gold*", Discussions of the Faraday Society 1951, 11, 55-75. According to this method, 200 ml of a 0.01% tetrachloroauric acid solution in water is heated to 100° C. under stirring, and 5 ml of a 1% trisodium citrate solution are subsequently added as a reducing agent. Once the nanoparticles are formed, the red-colored solution is left under stirring until reaching room temperature. Spherical gold nanoparticles having a diameter of 14-16 nm with a surface plasmon band at 519 nm are obtained.

Synthesis of triangular gold nanoprisms: The synthesis of triangular gold nanoprisms was carried out following the method described by Pelaz et al. "*Tailoring the synthesis and heating ability of gold nanoprisms for bioapplications*", Langmuir 2012, 28, 8965-70. According to this method, 100 ml of a 2 mM tetrachloroauric acid solution is mixed with 120 ml of a 0.5 mM $Na_2S_2O_3$ solution, leaving it under stirring for 9 minutes, after which a second addition of a volume between 20-50 ml of the 0.5 mM $Na_2S_2O_3$ solution is performed. Gold nanotriangles having a size comprised between 100-160 nm with a surface plasmon band between 750-1075 nm are obtained. Before conjugating them with different biomolecules, the nanoprisms must be passivated by means of binding with polyethylene glycol (HS-PEG-COOH, 5000 g/mol). To that end, 10 ml of the nanoprism solution is incubated with 1 mg of PEG in a NaOH solution, pH 12, overnight. Finally, these nanoprisms are centrifuged for 15 minutes at 10,000 rpm to remove excess reagents.

Synthesis of triangular silver nanoprisms: The synthesis was carried out following the method described by Zhang, Q et al, "*A systematic study of the synthesis of silver nanoplates: Is citrate a "Magic" reagent?*", Journal of the American Chemical Society 2011, 133 (46), 18931-18939. According to this method, 24.14 mL of Milli Q water is added to an aqueous solution of silver nitrate (0.05 M, 50 uL), trisodium citrate (75 mM, 0.5 mL), and hydrogen peroxide (30% wt, 60 uL) and are mixed by stirring vigorously at room temperature. Finally, a sodium borohydride solution ($NaBH_4$, 100 mM, 250 uL) is quickly added to form these nanoprisms. After about 3 minutes, the colloidal solution changes from a dark yellow color due to the formation of small silver particles to a bluish color generated by the final nanoprisms. Silver nanotriangles of 70 nm having a surface plasmon band at 700 nm are obtained.

Synthesis of copper nanocubes: The synthesis was carried out following the method described by Murphy et al. "Solution-phase synthesis of $Cu_2O$ nanocubes", Nano Letters 2002, 3 (2), 231-234. According to this method, 0.25 mL of an aqueous $CuSO_4$ solution are added to 9 mL of an aqueous CTAB (cetyl-trimethyl ammonium bromide) solution with a variable concentration of 0.01-0.1 M. Next, 0.5 mL of a 0.1 M aqueous sodium ascorbate solution are added to the Cu(II)-CTAB solution. The solutions were heated for 5 minutes at 55° C. Once this time has elapsed, 0.2 mL of 0.5 M sodium hydroxide are added, causing the immediate appearance of a yellow color in the solution. The solutions are maintained at 55° C. for 10 minutes and are left to cool at room temperature. After 30 minutes, the solutions turn a reddish brown, light yellow or dark yellow color depending on the concentration of CTAB used. The particles are centrifuged at 6000 rpm for 15 minutes and are then resuspended in water. This process is repeated twice to remove the surfactant. At this point the nanocubes in solution have a brick red color in all cases. Copper nanocubes with a size of about 420 nm, with different changes in their geometry according to the amount of the CTAB surfactant used in the synthesis are obtained.

Example 2

Functionalization of Metal Nanoparticles

Different types of nanoparticles synthesized with various recognition elements such as antibodies, DNA or PNA were functionalized to put the present invention into practice. Some examples of functionalization are described below.

Functionalization of triangular gold nanoprisms with antibodies: The functionalization was carried out by immobilizing the antibody on the carboxyl groups present on the surface of the nanoparticle through carbodiimide chemistry. First 0.5 mg of nanoparticle are activated with 1.5 µmoles of EDC and 3.5 µmoles of sulfo-NHS in a final volume of 1 ml of 10 mM MES, pH 6, for 30 minutes at 37° C. Excess reagents can be removed by centrifugation at 6000 rpm for 5 minutes, after which the particles are suspended in 10 mM MES, pH 6, or by means of using a gel filtration column. Once the carboxyl groups of the nanoparticles are activated, they are incubated with 2.5 µg of antibody in a final volume of 1 ml of 10 mM MES, pH 6, for 1 hour at 37° C. After the binding of the antibody, the surface of the nanoparticle is blocked with 50 mM 750 Da aminated PEG (α-methoxy-ω-amino polyethylene glycol). Finally, the nanoparticles are purified after several centrifugation cycles at 6000 rpm for 5 minutes.

Functionalization of triangular gold nanoprisms with streptavidin: The functionalization was carried out by immobilizing the streptavidin molecules on the carboxyl groups present on the surface of the nanoparticle through carbodiimide chemistry. First 0.5 mg of nanoparticles are activated with 1.5 umoles of EDC (1-ethyl-3-(3-dimethylaminopropyl) carbodiimide) and 3.5 umoles of sulfo-NHS (sulfo-N-hydroxysuccinimide) in a final volume of 1 ml of 10 mM MES, pH 6, for 30 minutes at 37° C. Excess reagents can be removed by centrifugation at 6000 rpm for 5 minutes, after which the particles are suspended in 10 mM MES, pH 6, or by means of using a gel filtration column. Once the carboxyl groups of the nanoparticles are activated, they are incubated with 1.25 µg of streptavidin in a final volume of 1 ml of 10 mM MES, pH 6, for 1 hour at 37° C. After the binding of the protein, the surface of the nanoparticle is blocked with 50 mM 750 Da aminated PEG (α-methoxy-ω-amino polyethylene glycol). Finally, the nanoparticles are purified after several centrifugation cycles at 6000 rpm for 5 minutes.

Example 3

Detection of the CEA Marker in a Sample Using the Biosensor of the Present Invention Once the gold nanoprisms are synthesized and characterized (both by scanning transmission electron microscopy and by ultraviolet-visible spectroscopy), they were functionalized with monoclonal anti-CEA antibodies, Ab3C6 (Monoclonal mouse anti-carcinoembryonic antigen 4CA30-3C6, HyTest) and also with the protein streptavidin. To verify that the molecules immobilized on the nanoprisms maintained their biological activity, the corresponding biomolecule was immobilized at different concentrations (the CEA marker or the biotin-conjugated antibody) on a nitrocellulose membrane; after incubating with the functionalized nanoparticles the membranes deposited on the heat sensitive surface were irradiated with the laser.

Figure 2A:
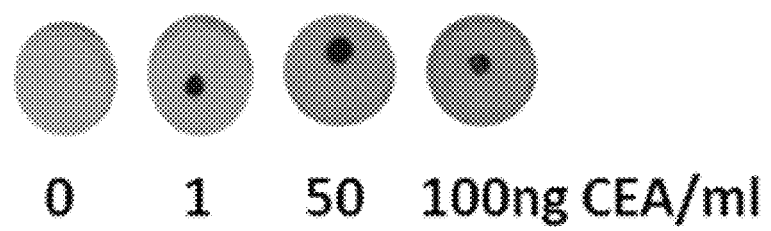
FIG. 2a shows CEA+anti-CEA antibody 3C6-nanoprisms recognition.

CEA+anti-CEA antibody 3C6-nanoprisms recognition is illustrated in FIG. 2a. Anti-CEA antibody 3C6-Biotin+Streptavidin-nanoprisms recognition is illustrated in FIG. 2b.

Figure 2B:
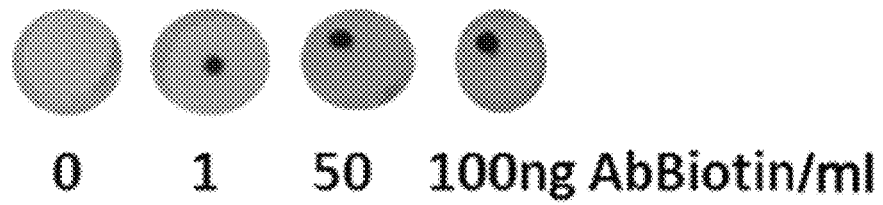
FIG. 2b shows the anti-CEA antibody 3C6-biotin+streptavidin-nanoprisms recognition.

When molecular recognition occurs, the gold nanoprisms are located on the membrane, and after being irradiated with the laser, the energy absorbed by the nanoparticles is released in the form of heat, a signal on the heat sensitive surface being recorded (see FIGS. 2a and 2b). In both cases, the signals obtained after irradiating the samples with the laser indicated that antigen-antibody or streptavidin-biotin recognition had occurred, and therefore the nanoprism-conjugated biomolecules maintained their activity. On the other hand, both the surfaces where recognition takes place and the surface of the nanoparticle had been passivated such that non-specific interactions did not occur when there is no protein immobilized on the nitrocellulose membrane, as can be seen in sample 0.

The recognition element of the sensor, in this case anti-CEA antibody Ab3C1, Monoclonal mouse anti-carcinoembryonic antigen 4CA30-3C1, HyTest, was immobilized on the sensing surface following various methodologies. It was bound to glass surfaces by means of covalent bonds as well as by means of physical adsorption on different cellulose and nitrocellulose membranes. The results obtained using nitrocellulose membranes with the antibody adsorbed on the surface are shown below. The two strategies described above were tested; the nanoprisms functionalized with the antibody directly were used and the nanoprisms functionalized with streptavidin after adding the anti-CEA biotin-conjugated antibody 3C6 were used. Different samples with a decreasing concentration of CEA tumor marker diluted in PBS were analyzed. After performing the steps of recognition described in the experimental method and once the membranes were dry, they were deposited on the heat sensitive surface, in this case on thermal paper, to be irradiated for a few seconds with a near infrared emitting laser (with a wavelength of 1000 nm).

Figure 3A:
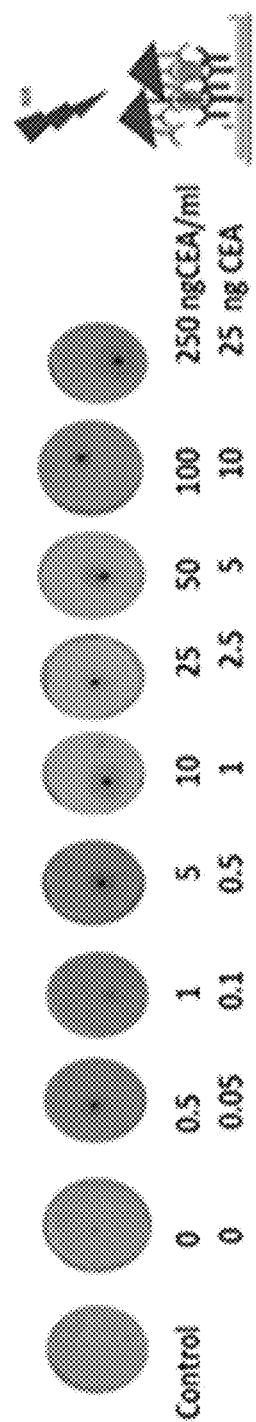
FIG. 3a shows anti-CEA antibody 3C1+CEA+anti-CEA antibody 3C6-nanoprisms recognition.
Figure 3B:
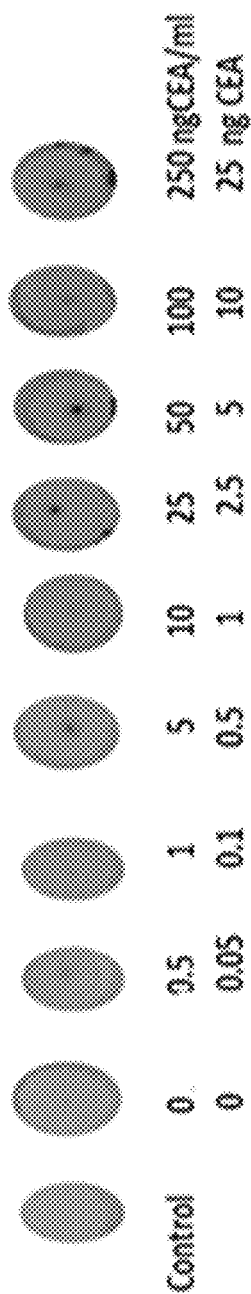
FIG. 3b shows anti-CEA antibody 3C1+CEA+anti-CEA antibody 3C6-biotin+streptavidin-nanoprisms recognition.

Anti-CEA antibody 3C1+CEA+anti-CEA antibody 3C6-Nanoprisms recognition is illustrated in FIG. 3a. Anti-CEA antibody 3C1+CEA+anti-CEA antibody 3C6-Biotin+Streptavidin-Nanoprisms recognition is illustrated in FIG. 3b.

Figure 4:
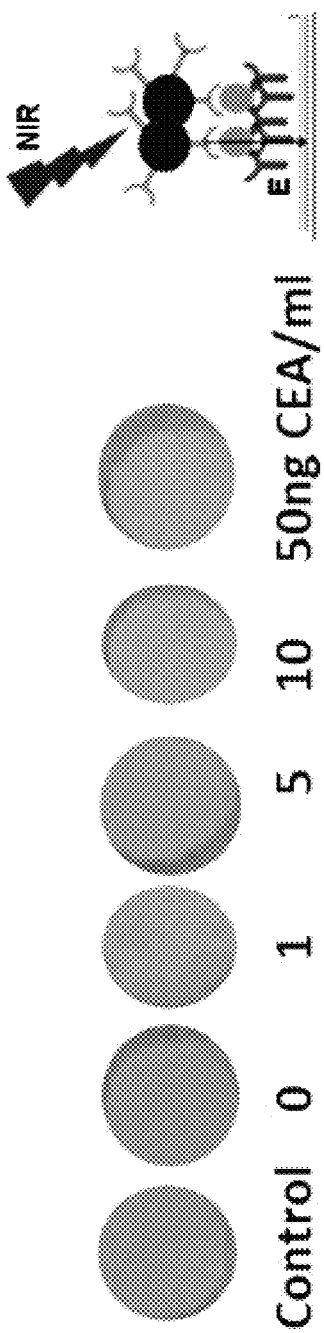
FIG. 4 shows anti-CEA antibody 3C1+CEA+anti-CEA antibody 3C6 gold nanoparticles recognition.

As can be seen in the preceding figures, the signal produced in the heat sensitive surface generated by irradiating the nanoprisms once analyte recognition occurs is more intense for the antibody 3C1-CEA-Ab3C6-nanoprism system than for the antibody 3C1-CEA-Ab3C6 Biotin-Streptavidin-gold nanoprism system. However, a concentration of 0.5 ng CEA/ml is detected in both cases. On the other hand, as a negative control, it was verified that when the same experiment is performed using spherical gold nanoparticles 16 nm in diameter functionalized with anti-CEA antibody 3C6 (which do not have an absorption band at the emission wavelength of the laser used), no signal was obtained, as shown in FIG. 4 (see FIG. 4 where anti-CEA antibody 3C1+CEA+anti-CEA antibody 3C6-Gold nanoparticles recognition is shown, where spherical gold nanoparticles 16 nm in diameter that do not have an absorption band at the emission wavelength of the laser used were used).

To improve method sensitivity, different parameters such as irradiation time of the sample with the laser and the distance of said laser from the sensing surface, can be varied. FIG. 5 shows how for a smaller distance between the laser and the surface, less irradiation time is needed and a more intense signal is obtained.

Figure 5A:
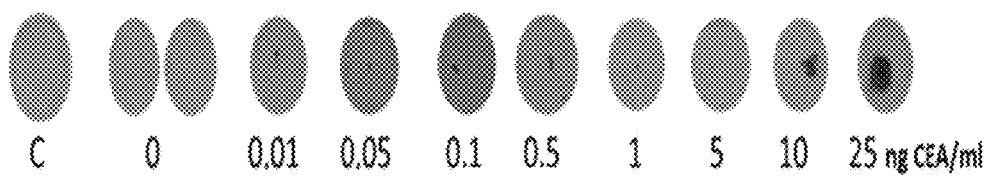
FIG. 5a shows the irradiation time of 10 seconds at a greater distance.
Figure 5B:
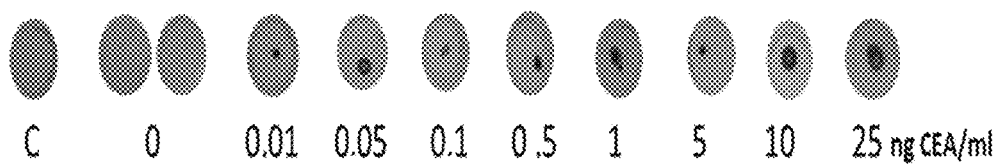
FIG. 5b shows the irradiation time of 2 seconds at a shorter distance.

FIG. 5 illustrates anti-CEA antibody 3C1+CEA+anti-CEA Ab3C6-gold nanoprisms recognition with different irradiation times and different distances between the surface and the laser. An irradiation time of 10 seconds at a distance of 0.5 cm is used in FIG. 5a; an irradiation time of 2 seconds at 0.1 cm is used in FIG. 5b.

Figure 6:
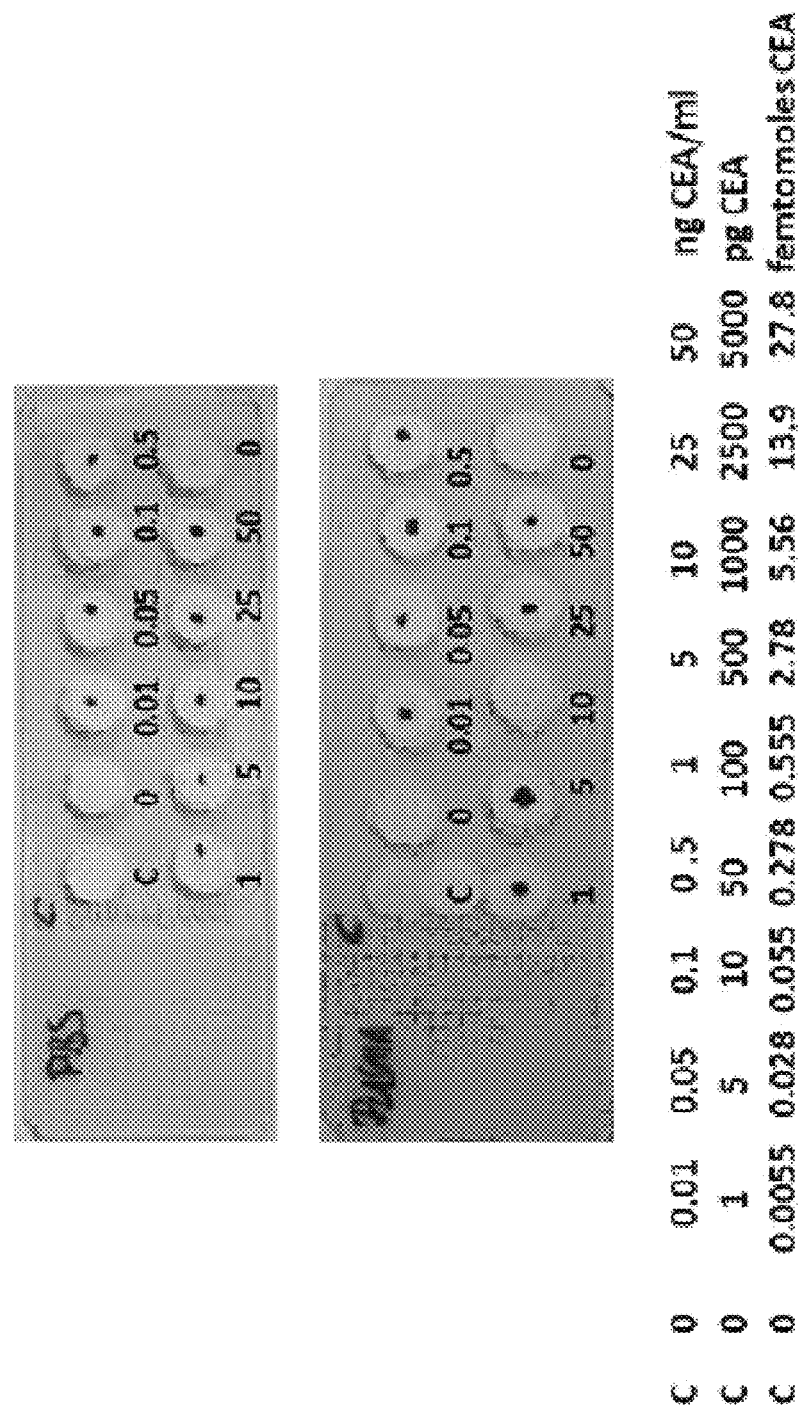
FIG. 6: shows anti-CEA antibody 3C1+CEA+anti-CEA antibody 3C6-nanoprisms recognition (in PBS buffer and in blood plasma samples).

Finally, the same "sandwich" type experiment (Ab3C1+CEA+Ab3C6-Gold nanoprisms) was carried out to detect the CEA tumor marker in blood plasma samples to verify system specificity as well as the detection limit of the analyte in a complex sample. It was compared with the results obtained for the determination of CEA dissolved in PBS buffer. A detection limit of 10 pg of CEA/ml was obtained in both cases, as can be seen in FIG. 6. Furthermore, no type of non-specific interaction was obtained in the control or in the plasma sample without CEA.

Example 4

Comparative Example Using an Infrared Camera as Detection Means

The same samples prepared for Example 3 were used for this experiment. The recognition element of the sensor, in this case anti-CEA antibody Ab3C1, was immobilized by means of physical adsorption on a nitrocellulose membrane. Different samples with a decreasing concentration of CEA tumor marker diluted in blood plasma were then analyzed. After performing the steps of recognition by means of the nanoparticles functionalized with the anti-CEA antibody Ab3C6 described in the experimental method and once the membranes were dry, they were deposited on thermal paper. A near infrared emitting laser at a wavelength of 1000 nm was used for irradiating the nanoparticles. An infrared thermal imaging camera (IR camera), capable of transforming the heat generated by the irradiated nanoparticles into a quantifiable measurement was used as a system for detecting the heat generated by the nanoparticles after being irradiated with the laser.

The temperature increase was verified with the IR camera after irradiating the samples prepared for detecting the blood plasma CEA antigen at different concentrations. After being irradiated for a few seconds with the laser, the IR camera recorded a temperature increase of 2-3° C. for the sample of 0.05 ng CEA/ml, but no signal was obtained in the case of the sample of 0.01 ng CEA/ml. For these same analyte concentrations a signal was detected in the case of thermal paper after the samples were irradiated with the laser.

A lower detection limit was obtained by means of visual detection using the support on a heat sensitive surface such as thermal paper than when using the infrared camera as the detection means.

Figure 7A:
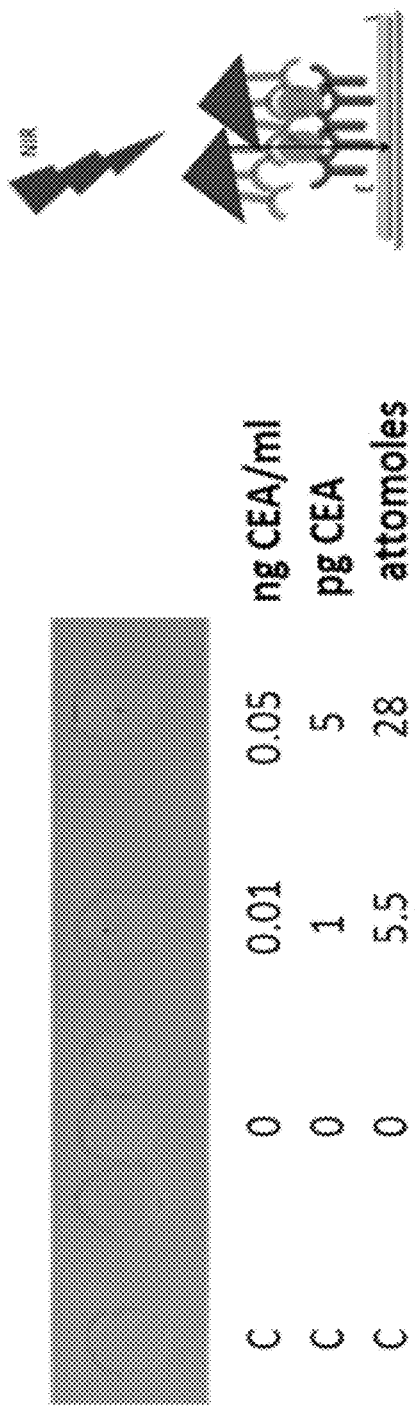
FIG. 7 shows anti-CEA antibody 3C1+CEA+anti-CEA antibody 3C6-gold nanoprisms recognition in blood plasma samples and detection by means of infrared camera.
Figure 7B:
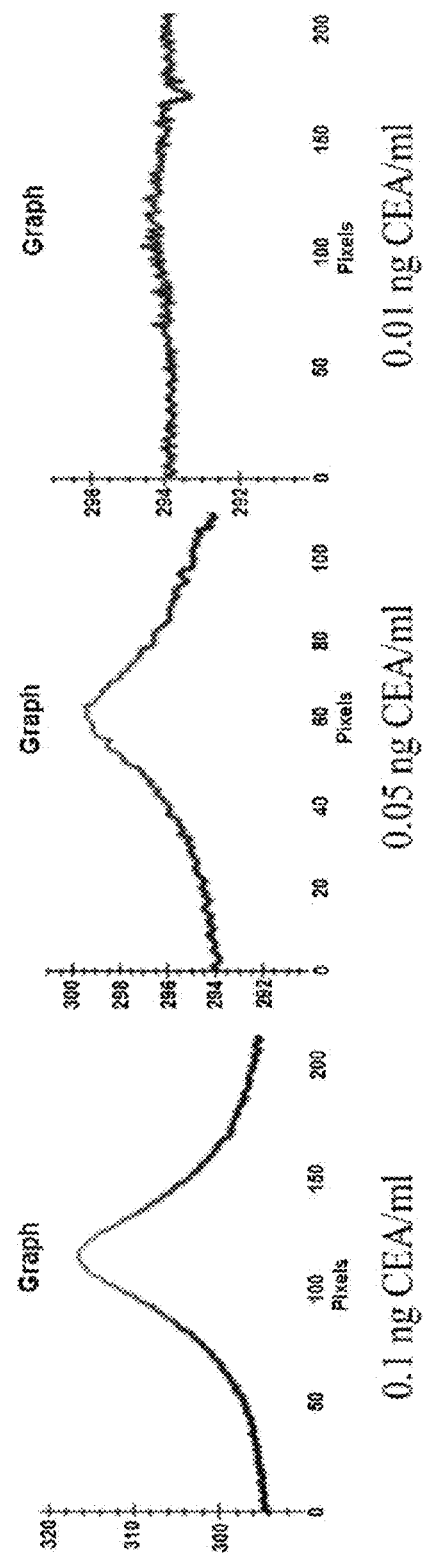

FIG. 7 compares the anti-CEA antibody 3C1+CEA+anti-CEA Ab 3C6-gold nanoprisms recognition between visual detection by means of thermal paper (FIG. 7a) and the IR camera as the detection system (FIG. 7b).

Example 5

Experiments of Detection with Thermopile

In this case the heat generated by the nanoparticles after being irradiated by the laser was measured by means of a thermopile capable of transforming the temperature increase generated in a specific area around it into a quantifiable electric signal.

With the design described in FIG. 8, (at a power of 350 mW) both the concentrated and the diluted samples were irradiated with the laser in the membrane and in the glass cover slip. The first problem that was encountered is that if the laser directly strikes the pile, a very high background signal is obtained (so it was necessary to increase the temperature enough to be distinguishable from the background signal). A response is also obtained if only the membrane or the cover slip without nanoparticles is irradiated (glass gives a higher signal than the nitrocellulose membrane). A response that was similar to the control was obtained with the diluted sample, whereas the temperature increase could be perfectly measured with the concentrated sample. It must be taken into account that in this design the sample was 3-4 cm away from the laser, so sensitivity is going to be lower than if it is directly in contact with the laser.

Calibration with different nanoparticle concentrations deposited on the nitrocellulose membrane for the designs depicted in FIG. 8, diagrams 2 and 3, was attempted. In the case of diagram 2, results were not obtained because the sample could not be irradiated in a reproducible manner with the laser in that position. The experiment was carried out with the design as indicated in diagram 3.

Three solutions of 140 µg/ml, 14 µg/ml and 1.4 µg/ml of NNs were prepared and 1 µl of each was deposited on nitrocellulose membranes (140 ng, 14 ng and 1.4 ng NNs→$6\times10^9$, $6\times10^8$ and $6\times10^7$ nanoparticles). They were irradiated with the laser for a few seconds and reading was performed with the thermopile before and after placing the sample. The background signal was recovered between samples. A signal that was somewhat higher than the background signal was recorded for the most diluted solution (1.4 ng NNs); a clearly distinguishable one was obtained with the 14 ng sample; the most concentrated sample yielded a very high signal. For a calibration that fits a linear range, a series of low concentration solutions would have to be used because after a certain concentration value, an exponential temperature increase is obtained with the nanoparticle concentration.

The invention claimed is:

1. A method for detecting an analyte in a sample, comprising the steps of:
   (a1) adding the sample comprising the analyte to a support with a first analyte recognition molecule immobilized thereon, wherein the support comprises a heat sensitive surface;
   (b1) incubating the support of step (a1) with metal nanoparticles functionalized with a second analyte recognition molecule; and
   (c1) irradiating the support of step (b1) with an external light source; or
   (a2) adding the sample comprising the analyte to a support with a first analyte recognition molecule immobilized thereon, wherein the support does not comprises a heat sensitive surface;
   (b2) incubating the support of step (a2) with metal nanoparticles functionalized with a second analyte recognition molecule;
   (c2) placing the support of step (b2) on a heat sensitive surface; and
   (d2) irradiating the support of step (c2) with an external light source.

2. The method of claim 1, wherein the analyte is an additive, a drug, a pathogenic microorganism, a food component, a pesticide, a toxic compound or oxygen.

3. The method of claim 1, wherein the analyte is visually detected by a color change in the support area where the analyte is present; and wherein the color change is produced as a result of heat generated by the metal nanoparticles when they are irradiated with the external light source.

4. The method of claim 1, wherein the heat sensitive surface comprises any surface capable of experiencing a structural change when heated, resulting in image development.

5. The method of claim 1, wherein the external light source is capable of causing excitation of surface plasmon absorption band of the metal nanoparticles.

6. The method of claim 4, wherein the external light source produces radiation of wavelength of between 750 nm and 110 nm.

7. The method of claim 4, wherein the external light source is a monochromatic or a polychromatic light source.

8. The method of claim 1, wherein the metal nanoparticles comprise gold, silver or copper.

9. The method of claim 1, wherein the heat sensitive surface is a thermal paper or a temperature sensitive polymer.

10. The method of claim 9, wherein the temperature sensitive polymer comprises poly(N-isopropylacrylamide), poly(N-vinylpiperidine) or poly(N-inylcaprolactam).

11. A method for detecting an analyte in a sample, comprising the steps of:
   (a3) adding the sample comprising the analyte to a support with a first analyte recognition molecule immobilized thereon, wherein the support comprises a heat sensitive surface;
   (b3) incubating the support of step (a3) with a second analyte recognition molecule bound to at least one label molecule;
   (c3) incubating the support of step (b3) with metal nanoparticles functionalized with at least one molecule capable of specifically binding to the label molecule; and
   (d3) irradiating the support of step (c3) with an external light source; or
   (a4) adding the sample comprising the analyte to a support with a first analyte recognition molecule immobilized thereon, wherein the support does not comprise a heat sensitive surface;
   (b4) incubating the support of step (a4) with a second analyte recognition molecule bound to at least one label molecule;
   (c4) incubating the support of step (b4) with metal nanoparticles functionalized with at least one molecule capable of specifically binding to the label molecule;
   (d4) placing the support of step (c4) on a heat sensitive surface; and
   (d4). irradiating the support of step (d4) with an external light source.

12. The method of step 11, wherein the analyte is visually detected by a color change in the support area where the analyte is present; and wherein the color change is produced as a result of heat generated by the metal nanoparticles when they are irradiated with the external light source.

13. The method of claim 11, wherein the label molecule is biotin and wherein the at least one molecule capable of specifically binding the label molecule is avidin or streptavidin; or wherein the label molecule is avidin or streptavidin and the at least one molecule capable of specifically binding the label molecule is biotin.

14. The method of claim 11, wherein the heat sensitive surface comprises any surface capable of experiencing a structural change when heated, resulting in image development.

15. The method of claim 11, wherein the external light source is capable of causing excitation of surface plasmon absorption band of the metal nanoparticles.

16. The method of claim 14, wherein the external light source produces radiation of wavelength of between 750 nm and 110 nm.

17. The method of claim 14, wherein the external light source is a monochromatic or a polychromatic light source.

18. The method of claim 11, wherein the metal nanoparticles comprise gold, silver or copper.

19. The method of claim 11, wherein the heat sensitive surface is a thermal paper or a temperature sensitive polymer.

20. The method of claim 19, wherein the temperature sensitive polymer comprises poly(N-isopropylacrylamide), poly(N-vinylpiperidine) or poly(N-vinylcaprolactam).

21. The method of claim 11, wherein the analyte is an additive, a drug, a pathogenic microorganism, a food component, a pesticide, a toxic compound or oxygen.

* * * * *

UNITED STATES PATENT AND TRADEMARK OFFICE
CERTIFICATE OF CORRECTION

PATENT NO. : 10,197,566 B2
APPLICATION NO. : 14/417006
DATED : February 5, 2019
INVENTOR(S) : Pablo Del Pino González De La Higuera et al.

It is certified that error appears in the above-identified patent and that said Letters Patent is hereby corrected as shown below:

In the Claims

At Column 19, Claim number 10, Line number 51, replace the term "poly(N-inylcaprolactam)" with --poly(N-vinylcaprolactam).--

Signed and Sealed this
Thirteenth Day of August, 2019

Andrei Iancu
*Director of the United States Patent and Trademark Office*